US011166946B2

(12) United States Patent
Pause

(10) Patent No.: US 11,166,946 B2
(45) Date of Patent: Nov. 9, 2021

(54) DOSAGE REGIMEN FOR PICOTAMIDE FOR THE USE IN MIGRAINE

(71) Applicant: CURATIS AG, Liestal (CH)

(72) Inventor: Arnim Pause, Montreal (CA)

(73) Assignee: CURATIS AG, Liestal (CH)

(*) Notice: Subject to any disclaimer, the term of this patent is extended or adjusted under 35 U.S.C. 154(b) by 0 days.

(21) Appl. No.: 16/949,866

(22) Filed: Nov. 18, 2020

(65) Prior Publication Data
US 2021/0069160 A1  Mar. 11, 2021

Related U.S. Application Data

(63) Continuation of application No. PCT/EP2018/064381, filed on May 31, 2018.

(51) Int. Cl.
*A61K 31/444* (2006.01)
*A61P 25/06* (2006.01)
*A61K 9/00* (2006.01)

(52) U.S. Cl.
CPC ........... *A61K 31/444* (2013.01); *A61K 9/009* (2013.01); *A61K 9/0056* (2013.01); *A61P 25/06* (2018.01)

(58) Field of Classification Search
CPC .............................. A61K 31/444; A61P 25/06
See application file for complete search history.

(56) References Cited

U.S. PATENT DOCUMENTS

2009/0004121 A1  1/2009 Kempen

FOREIGN PATENT DOCUMENTS

WO   2008/142106   11/2008
WO   2018/104235    6/2018

OTHER PUBLICATIONS

International Search Report dated Feb. 12, 2019 in PCT/EP2018/064381.
Written Opinion dated Feb. 12, 2019 in PCT/EP2018/064381.
Allais et al., "Picotamide in migraine aura prevention: a pilot study," Neurol Sci (2004) 25:S267-S269.
Castellani et al., "Thromboxane Inhibition Improves Renal Perfusion and Excretory Function in Severe Congestive Heart Failure," J Am Coll Cardiol 2003;42:133-9.
Cattaneo et al., "In Vitro Effects of Picotamide on Human Platelet Aggregation, the Release Reaction and Thromboxane $B_2$ Production," Thrombosis Research 62; 717-724, 1991.
Cocozza et al., "Effects of Picotamide, and Antithromboxane Agent, on Carotid Atherosclerotic Evolution," Stroke, vol. 26, Issue 4, Apr. 1995, pp. 597-601, 30 pages.
Cucchiara et al., "Migraine and circle of Willis anomalies," Medical Hypotheses (2008) 70, 860-865.
D'Andrea et al., "Migraine with aura: conventional and non-conventional treatments," Neurol Sci (2011) 32 (Suppl 1):S121-S129.
Ertas et al., "One-year prevalence and the impact of migraine and tension-type headache in Turkey: a nationwide home-based study in adults," J Headache Pain (2012) 13:147-157.
Fendrich et al., "Headache prevalence among adolescents—the German DMKG headache study," Cephalalgia, 2007, 27, 347-354.
Gresele et al., "Characterization of N,N'-bis(3-Picolyl )-4-Methoxy-Isophtalamide (Picotamide) as a Dual Thromboxane Synthase Inhibitor/ Thromboxane $A_2$ Receptor Angatonist in Human Platelets," Thrombosis and Haemostasis 61 (3) 479-484 (1989).
"Guideline on Clinical Investigation of Medicinal Products for the Treatment of Migraine," European Medicines Agency, Evaluation of Medicines for Human Use, Committee for Medicinal Products for Human Use (CHMP), Jan. 24, 2007, 12 pages.
Hildreth et al., "Migraine Headache," JAMA, Jun. 24, 2009—vol. 301, No. 24, p. 2608.
Kirchmann et al., "Basilar-type migraine," Neurology 2006;66:880-886.
Le et al., "Increase in self-reported migraine prevalence in the Danish adult population: a prospective longitudinal population-based study," BMJ Open, 2012;2;e000962, pp. 1-7.
Neri Serneri at al., "Pathophysiology and Natural History, The role of extraplatelet thromboxane $A_2$ in unstable angina investigated with a dual thromboxane A2 inhibitor: importance of activated monocytes," Coronary Artery Disease 1994; 5:137-145.
Neri Serneri et al., "Picotamide, a combined inhibitor of thromboxane A2 synthase and receptor, reduces 2-year mortality in diabetics with peripheral arterial disease: the DAVID study," European Heart Journal (2004) 25, 1845-1852.
Oleson et al., "The International Classification of Headache Disorders 3rd edition (beta version)," Cephalalgia, International Headache Society, 2013, 33(9) 629-808.
Pardutz et al., "NSAIDs in the Acute Treatment of Migraine: A Review of Clinical and Experimental Data," Pharmaceuticals 2010, 3, 1966-1987.
Pietrobon et al., "Neurobiology of Migraine," Nat Rev Neurosci. May 2003;4(5):386-98.

(Continued)

Primary Examiner — Kevin E Weddington
(74) Attorney, Agent, or Firm — Grüneberg and Myers PLLC

(57) ABSTRACT

Picotamide (4-methoxy-N,N'-bis(pyridin-3-ylmethyl)benzene-1,3-dicarboxamide, CAS-no. 32828-81-2) can be used in the treatment and/or prevention of migraine with aura. A specific dosage regimen is used in this treatment and/or prevention, where, in a first period, picotamide is administered for 2 to 6 months, and the first period is followed by a second period of 1 to 3 months without picotamide administration.

17 Claims, 1 Drawing Sheet

(56) References Cited

OTHER PUBLICATIONS

Violi et al., "*Safety of Picotamide, an Antiplatelet Agent, in an 18-Month, Double-Blind, Placebo-Controlled, Multicenter Trial in 2304 Patients With Peripheral Vascular Disease*," Current Therapeutic Research, vol. 54, No. 1, Jul. 1993, pp. 111-121.

Ying et al., "*Clinical Characteristics of Basilar-Type Migraine in the Neurological Clinic of a University Hospital*," Headache & Facial Pain Section, Pain Medicine 2014; 15: 1230-1235.

Yong et al., "*Prevalence and risk factors for depression and anxiety among outpatient migraineurs in mainland China*," J Headache Pain (2012) 13:303-310.

Yoon et al., "*Prevalence of primary headaches in Germany: results of the German Headache Consortium Study*," J Headache Pain (2012) 13:215-223.

DOSAGE REGIMEN FOR PICOTAMIDE FOR THE USE IN MIGRAINE

CROSS-REFERENCE TO RELATED APPLICATIONS

The present application is a continuation of the International Application PCT/EP2018/064381, filed May 31, 2018, the entirety of which is hereby incorporated by reference.

BACKGROUND OF THE INVENTION

Field of the Invention

The present invention relates to picotamide (4-methoxy-N,N'-bis(pyridin-3-ylmethyl)benzene-1,3-dicarboxamide, CAS-no. 32828-81-2) for use in the treatment and/or prevention of migraine with aura by using a specific dosage regimen.

Description of the Related Art

Picotamide (INN, International Nonproprietary Name), denotes the compound 4-methoxy-N,N'-bis(pyridin-3-ylmethyl)benzene-1,3-dicarboxamide (IUPAC), CAS-No. 32828-81-2, with the following structure:

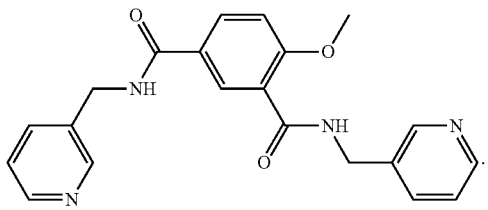 [SMILES: COc1ccc(C(=O)NCc2cccnc2)cc1C(=O)NCc1cccnc1]

Picotamide is usually applied as monohydrate. However, pharmaceutically acceptable salts have also been described (WO2008/142106).

Picotamide has a pharmacological profile characterized by antiplatelet and fibrinolytic activity. It is marketed as Plactidil® in Italy for the treatment of thromboembolic disorders, in which an inhibition of platelet reactivity and activation of the fibrinolytic potential is indicated, i.e. myocardial infarction, venous thrombosis and arterial cerebrovascular disorders, pulmonary embolism and atherosclerotic states in general.

Picotamide is a dual $TxA_2$-synthase inhibitor/thromboxane endoperoxide receptor antagonist, which inhibits in vitro platelet aggregation, degranulation, and $TxB_2$ production, in a dose dependent manner (Gresele et al., Thromb Haemost. 1989; 61:479-84; Cattaneo et al., Thromb Res. 1991; 62:717-724).

Moreover, picotamide is able to block platelet aggregation induced by arachidonic acid (AA), collagen and adenosine 5'-diphosphate (ADP) in vitro and ex vivo; and increases fibrinolysis. The anti-platelet efficacy is further potentiated by an increased production of prostacyclin by endothelial cells/vessel wall by the diversion of AA toward prostacyclin ($PGI_2$) formation. Picotamide seems to block the pro-aggregatory and vasoconstrictive effects of serotonin and adrenalin.

After oral administration, picotamide monohydrate is rapidly absorbed from the gastrointestinal (GI) tract and reaches its peak concentration in the plasma within one hour. Its plasma clearance is biphasic with a half-life of about 2 hours for the first rapid phase. The second phase clearance is slower. Binding of picotamide to platelets is initially reversible, but rapidly becomes irreversible. Inhibition of platelet aggregation persists upon washing out the drug. Picotamide is able to downregulate thromboxane receptors in platelets in the 2-4 hour period after oral dosing. Picotamide accumulates in plasma membrane of the platelets (and possibly in other blood cells), which may contribute to the long duration of the second phase of plasma clearance. Its elimination is mainly via the urinary tract.

Acute, subacute and chronic toxicity studies have been performed in the mouse, rat and dog by intraperitoneal (IP) and oral (PO) administration routes. The $LD_{50}$ values in the mouse were 942±29 mg/kg (IP) and >3,000 mg/kg (PO). In the rat the same values were 685±27 mg/kg (IP) and >3,000 mg/kg (PO). The substance was well tolerated after subacute and chronic treatment, and did not induce embryotoxic or teratogenic effects.

Following single administration of picotamide (300 mg) in human subjects the time to reach maximum concentration ($T_{max}$) was in the range of 0.5-0.75 h. The elimination is mainly via urine soon after the 3rd hour of treatment. Repeated administration does not result in accumulation.

Picotamide has been tried in numerous human clinical studies including two large multicenter trials. In a double-blind, placebo-controlled, multicenter clinical trial, 2,304 patients with peripheral vascular disease were included to assess the effectiveness and safety of picotamide (300 mg, PO, t.i.d.) for an 18-month period (ADEP study; Violi et al., Current Ther Res 1993, 54:111-121). Picotamide was shown to be an effective and well-tolerated antiplatelet drug with an incidence of adverse reactions similar to that of placebo. In another multicenter, randomized, double blind trial, the effect of picotamide was favorably compared with aspirin for the prevention of mortality and major cardiovascular events in 1209 adult diabetic patients with peripheral arterial disease (DAVID study; Neri Serneri et al., Eur Heart J 2004; 25:1845-1852).

Picotamide has been demonstrated to be effective in primary prevention of cardiovascular (CV) events in patients with peripheral arterial disease (PAD); in secondary prevention of transient ischemic attack (TIA) and stroke. In comparative clinical trials, picotamide was superior to aspirin in reducing anginal events in patients with unstable angina (Neri Serneri at al., Coronary Artery Dis. 1994; 5:137-145); reducing recurrent cardiovascular disease (CVD) events in patients with acute myocardial infarction; reducing the total mortality in patients with PAD and diabetes after 2 year treatment; reducing albuminuria in patients with microalbuminuria; reducing progression of plaques in carotid arteries in diabetic patients (Cocozza et al., Stroke, 1995, 26:597-601); reducing serum creatinine and pulmonary pressure in congestive heart failure (CHF) patients (Castellani et al., J Am Coll Cardiol 2003; 42:133-139); and reducing aura in migraine patients (G. Allais et al, Neurol. Sci. (2004) 25: S267-S269).

Tolerance to picotamide demonstrated both during clinical trials and over its marketing history has been good. No serious side effects have ever been reported.

Migraine is a common disabling primary headache disorder. Epidemiological studies have documented its high prevalence and high socio-economic and personal impacts all over the world (Fendrich et al., Cephalalgia, 2007; 27:347-54; Le et al., BMJ Open, 2012; 2(4); Yong et al., J Headache Pain. 2012; 13:303-10; Yoon et al., J Headache Pain. 2012; 13:215-23; Ertas et al., J Headache Pain. 2012;

13:147-57). Migraine is now ranked by the World Health Organization as number 19 among all diseases world-wide causing disability. Commonly starting at puberty, migraine most affects those aged between 20 and 50 years but can trouble much younger people, including children. The one-year prevalence in adults is estimated to be 15%. In children and adolescents, the prevalence is approximately 5%. European and American studies have shown that 6-8% of men and 15-18% of women experience migraine each year. The higher rates in women everywhere (2-3 times those in men) are hormonally-driven. Prevalence declines after 50 years of age (WHO Fact Sheet No 277, 2004; EMA CHMP Guideline, 2007).

There is no absolute cure for migraine since its pathophysiology has yet to be fully understood (Pietrobon & Striessnig, Nat Rev Neurosci. 2003; 4:386-98; Cucchiara & Detre, Med Hypotheses. 2008; 70:860-5). There are two medication strategies for treating migraine headaches. Treating the pain at the onset offers the best relief. Over-the-counter pain relievers such as acetaminophen, aspirin or other nonsteroidal anti-inflammatory drugs (NSAIDs) such as ibuprofen are commonly used (Pardutz & Schoenen, Pharmaceuticals. 2010; 3:1966-1987). Prescription drugs such as triptans are used for headaches not relieved by over-the-counter medications. These are generally not applied to people who have high blood pressure or a heart disease. For those whose headaches are not adequately relieved with these medications, the second medication strategy involves medications prescribed prophylactically. These are normally prescribed to treat other disorders but have been successful at reducing the frequency or severity of migraine headaches. Blood pressure medications such as beta-blockers or calcium channel blockers, antidepressant medications such as amitriptyline or venlafaxine, and anticonvulsant medications such as divalproex or topiramate (Hildreth et al., JAMA. 2009; 301:2608) have been used.

Summarizing the above, there is a need for adequate and safe migraine treatment and prophylaxis.

SUMMARY OF THE INVENTION

It is therefore an object of the present invention to provide a medication for the treatment and/or the prevention of migraine with aura.

The present inventors have recognized that the platelet aggregation inhibitor picotamide may be used for the treatment and for the prevention of migraine aura, notably migraine with aura.

Thus, this and other objects of the invention have been achieved by the present invention, the scope of which includes picotamide, a hydrate, or a pharmaceutically acceptable salt thereof, and the use thereof in the treatment and/or prevention of migraine with aura, wherein in a first period picotamide is administered for 2 to 6 months, followed by a second period of 1 to 3 months without picotamide administration.

The present invention includes the following embodiments below:

1. Picotamide, a hydrate or a pharmaceutically acceptable salt thereof for use in the treatment and/or prevention of migraine with aura, wherein in a first period picotamide is administered for 2 to 6 months, followed by a second period of 1 to 3 months without picotamide administration.
2. Picotamide, a hydrate or a pharmaceutically acceptable salt thereof for the use according to embodiment 1, wherein the sequence of period 1 followed by period 2 is repeated.
3. Picotamide, a hydrate or a pharmaceutically acceptable salt thereof for the use according to embodiments 1 or 2, wherein period 1 is longer than period 2.
4. Picotamide, a hydrate or a pharmaceutically acceptable salt thereof for the use according to any one of embodiments 1 to 3, wherein the migraine with aura is in the range of 3 to 6 aura attacks per months.
5. Picotamide, a hydrate or a pharmaceutically acceptable salt thereof for the use according to any one of embodiments 1 to 4, wherein the migraine with aura is migraine with typical aura.
6. Picotamide, a hydrate or a pharmaceutically acceptable salt thereof for the use according to any one of embodiments 1 to 4, wherein the migraine with aura is hemiplegic migraine.
7. Picotamide, a hydrate or a pharmaceutically acceptable salt thereof for the use according to any one of embodiments 1 to 4, wherein the migraine with aura is migraine with brainstem aura.
8. Picotamide for use according to any one of embodiments 1 to 6, wherein picotamide is a monohydrate.
9. Picotamide for use according to any one of embodiments 1 to 6, wherein the pharmaceutically acceptable salt is picotamide hydrochloride or picotamide mesylate.
10. Picotamide, a hydrate or a pharmaceutically acceptable salt thereof for use according to any one of embodiments 1 to 9, wherein the treatment dosage is from 200 to 1300 mg based on free base anhydride per day.
11. Picotamide, a hydrate or a pharmaceutically acceptable salt thereof for use according to any one of embodiments 1 to 9, wherein the treatment dosage is from 200 to 1300 mg free base anhydride in a sustained release form.
12. Picotamide, a hydrate or a pharmaceutically acceptable salt thereof for use according to any one of embodiments 1 to 9, wherein the treatment dosage is from 200 to 1300 mg free base anhydride provided in a sachet, an orally disintegrating tablet, a chewing tablet, or a lozenge.
13. Picotamide, a hydrate or a pharmaceutically acceptable salt thereof for use according to any one of embodiments 1 to 11, wherein the treatment dosage is a once per day dosage.
14. A pharmaceutical composition comprising picotamide, a hydrate or a pharmaceutically acceptable salt thereof for the use according to any one of embodiments 1 to 7.
15. A pharmaceutical composition according to embodiment 14, wherein picotamide is contained from 200 to 1300 mg based on free base anhydride.
16. A method of treatment and/or prevention of migraine with aura, said method comprising:
   administering, in a first period, picotamide, a hydrate or a pharmaceutically acceptable salt thereof for 2 to 6 months, followed by a second period of 1 to 3 months without picotamide administration.
17. Use of picotamide, a hydrate or a pharmaceutically acceptable salt thereof for the manufacture of a pharmaceutical composition for the use in the treatment or prevention of migraine with aura, wherein in a first period picotamide is administered for 2 to 6 months, followed by a second period of 1 to 3 months without picotamide administration.

DETAILED DESCRIPTION OF THE INVENTION

Figure 1:
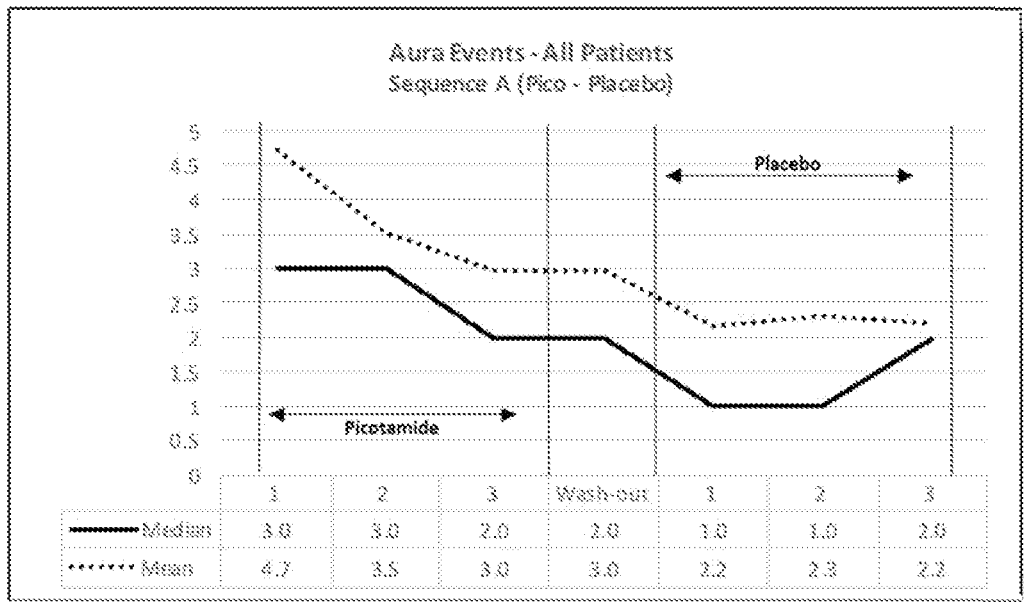
FIG. 1 shows a sequence A, all patients having 1 to 28 aura events per month.

Any ranges mentioned herein below include all values and subvalues between the lowest and highest limit of this range, including the limits.

The present invention relates to embodiments as described herein. Thereby, the following definitions are used:

Several forms of migraine are known and can be diagnosed specifically (see "The International Classification of Headache Disorders", 3rd edition: Cephalalgia 33(9) 629-808).

(a) In the present invention, the term "migraine with aura" encompasses in particular migraine with typical aura, but also hemiplegic migraine, migraine with brainstem aura, and moderate migraine with aura.

(b) In the present invention, the term "migraine headache" relates to headache attacks, which are accompanied with aura or follow after aura.

(c) In the present invention, the term "migraine with aura" denotes migraine with recurrent attacks lasting minutes, of unilateral fully reversible visual, sensory or other central nervous system symptoms that usually develop gradually and are usually followed by headache and associated migraine symptoms. Diagnostic criteria for a definition are:
  A. At least two attacks fulfilling criteria B and C:
  B. One or more of the following fully reversible aura symptoms:
    1. visual;
    2. sensory;
    3. speech and/or language;
    4. motor;
    5. brainstem;
    6. retinal;
  C. At least two of the following four characteristics:
    1. at least one aura symptom spreads gradually over ≥5 minutes, and/or two or more symptoms occur in succession;
    2. each individual aura symptom lasts 5-60 minutes;
    3. at least one aura symptom is unilateral;
    4. the aura is accompanied, or followed within 60 minutes, by headache.

When, for example, three symptoms occur during an aura, the acceptable maximal duration is 3×60 minutes. Motor symptoms may last up to 72 hours. Aphasia is always regarded as a unilateral symptom; dysarthria may or may not be.

In a further embodiment, patients are required to have at least one aura a month.

The term "migraine headache" or headache in combination with migraine with aura means a recurrent headache manifesting in attacks lasting 4-72 hours. Typical characteristics of the headache are unilateral location, pulsating quality, moderate or severe intensity, aggravation by routine physical activity and association with nausea and/or photophobia and phonophobia. Diagnostic criteria for a definition are:
  [A.] At least five attacks fulfilling criteria [B]-[D]:
  [B.] Headache attacks lasting 4-72 hours (untreated or unsuccessfully treated);
  [C.] Headache has at least two of the following four characteristics:
    [1.] unilateral location;
    [2.] pulsating quality;
    [3.] moderate or severe pain intensity;
    [4.] aggravation by routine physical activity (e.g. walking or climbing stairs);
  [D.] During headache at least one of the following:
    [1.] nausea and/or vomiting;
    [2.] photophobia and phonophobia.

(d) In the present invention, the term "migraine with typical aura" denotes migraine with aura in which aura consists of visual and/or sensory and/or speech/language symptoms, but no motor weakness, and is characterized by gradual development, duration of each symptom no longer than 1 hour and complete reversibility. Diagnostic criteria for a definition are:
  A. At least two attacks fulfilling criteria B and C:
  B. Aura consisting of visual, sensory and/or speech/language symptoms, each fully reversible, but no motor, brainstem or retinal symptoms;
  C. At least two of the following four characteristics:
    1. at least one aura symptom spreads gradually over ≥5 minutes, and/or two or more symptoms occur in succession;
    2. each individual aura symptom lasts 5-60 minutes;
    3. at least one aura symptom is unilateral;
    4. the aura is accompanied, or followed within 60 minutes, by headache.

The term "migraine headache" or headache in combination with migraine with typical aura is the same as described above in point (c).

Visual aura is the most common type of aura. It often presents as a fortification spectrum: a zigzag figure near the point of fixation that may gradually spread right or left and assume a laterally convex shape with an angulated scintillating edge, leaving absolute or variable degrees of relative scotoma in its wake. In other cases, scotoma without positive phenomena may occur; this is often perceived as being of acute onset but, on scrutiny, usually enlarges gradually.

Next in frequency are sensory disturbances, in the form of pins and needles moving slowly from the point of origin and affecting a greater or smaller part of one side of the body, face and/or tongue. Numbness may occur in its wake, but numbness may also be the only symptom.

Less frequent are speech disturbances, usually aphasic but often hard to categorize (see Cephalalgia 33(9) 629-808).

When the aura includes motor weakness, the disorder should be coded as hemiplegic migraine or one of its subforms.

Aura symptoms of these different types usually follow one another in succession, beginning with visual, then sensory, then aphasic; but the reverse and other orders have been noted. The accepted duration for most aura symptoms is 1 hour, but motor symptoms are often longer lasting.

Systematic studies have demonstrated that many patients with visual aura occasionally have symptoms in the extremities and/or speech symptoms. Conversely, patients with symptoms in the extremities and/or speech or language symptoms almost always also experience visual aura symptoms at least during some attacks. A distinction between migraine with visual aura, migraine with hemiparaesthetic aura and migraine with speech and/or language aura is probably artificial, and therefore is not recognized in this classification. They are all coded as migraine with typical aura. Patients with aura symptoms arising from the brainstem are coded as migraine with brainstem aura, but they almost always have additional typical aura symptoms. Patients with hemiplegic migraine have motor weakness, and this is classified as a separate subform because of genetic and pathophysiological differences from migraine with typical aura. Such patients often have brainstem symptoms in addition (see Cephalalgia 33(9) 629-808).

(e) In the present invention, the term "hemiplegic migraine" means migraine with aura including motor weakness. Diagnostic criteria for a definition are:

A. At least two attacks fulfilling criteria B and C:
B. Aura consisting of both of the following:
  1. fully reversible motor weakness;
  2. fully reversible visual, sensory and/or speech/language symptoms;
C. At least two of the following four characteristics:
  1. at least one aura symptom spreads gradually over ≥5 minutes, and/or two or more symptoms occur in succession;
  2. each individual non-motor aura symptom lasts 5-60 minutes, and motor symptoms last <72 hours;
  3. at least one aura symptom is unilateral;
  4. the aura is accompanied, or followed within 60 minutes, by headache.

The term "migraine headache" or headache in combination with migraine with typical aura is the same as described above in point (c).

Hemiplegic migraine (HM) is a rare variety of migraine with aura characterized by the presence of a motor weakness during the aura. Hemiplegic migraine has two main forms depending on the familial history: patients with at least one first- or second-degree relative who has aura including motor weakness have familial hemiplegic migraine (FHM); patients without such familial history have sporadic hemiplegic migraine (SHM). Severe attacks may occur in both FHM and SHM with prolonged hemiplegia, confusion, coma, fever and seizures. The clinical spectrum also includes permanent cerebellar signs (nystagmus, ataxia, dysarthria) and less frequently various types of seizures and intellectual deficit. The prevalence of HM is one in 10,000, with FHM and SHM being equally frequent.

The present invention shall be focused on FHM. There are 3 known loci for FHM. FHM1, which accounts for approximately 50% of FHM patients, is caused by mutations in a gene coding for the P/Q-type calcium channel a subunit, CACNA1A. FHM1 is also associated with cerebellar degeneration.

FHM2, which accounts for <25% of FHM cases, is caused by mutations in the Na+/K+-ATPase gene ATP1A2. FHM3 is a rare subtype of FHM and is caused by mutations in a sodium channel α-subunit coding gene, SCN1A. A fourth gene that has been associated with this condition is the proline rich transmembrane protein 2 (PRRT2), an axonal protein associated with the exocytosis complex. A fifth gene associated with this condition is SLC4A4 which encodes the electrogenic NaHCO3 cotransporter NBCe1.

Hence, present invention sets its focus on FHM caused by defects in CACNA1A, Na+/K+-ATPase gene ATP1A2, SCN1A, SLC4A4, and PRRT2.

(f) In the present invention, the term "migraine with brainstem aura" denotes a migraine with aura symptoms clearly originating from the brainstem, but no motor weakness. Diagnostic criteria for a definition are:

A. At least two attacks fulfilling criteria B-D:
B. Aura consisting of visual, sensory and/or speech/language symptoms, each fully reversible, but no motor or retinal symptoms:
C. At least two of the following brainstem symptoms:
  1. dysarthria;
  2. vertigo;
  3. tinnitus;
  4. hypacusis;
  5. diplopia;
  6. ataxia;
  7. decreased level of consciousness;
D. At least two of the following four characteristics:
  1. at least one aura symptom spreads gradually over ≥5 minutes, and/or two or more symptoms occur in succession;
  2. each individual aura symptom lasts 5-60 minutes;
  3. at least one aura symptom is unilateral;
  4. the aura is accompanied, or followed within 60 minutes, by headache.

Thereby, aphasia is always regarded as a unilateral symptom; dysarthria may or may not be.

The term "migraine headache" or headache in combination with migraine with typical aura is the same as described above in point (c).

Migraine with brainstem aura (MBA) is characterized by recurring attacks of certain temporary symptoms that are believed to originate in the brainstem. The brainstem is located at the base of the brain and connects to the top of the spinal cord; its function is to help regulate the two-way channel of communication between the brain and the body. Until 2013, MBA was known as "basilar-type migraine". In the updated version of the International Headache Society's guidelines—The International Classification of Headache Disorders, 3rd Edition, Cephalalgia 33(9) 629-808—it was renamed "migraine with brainstem aura" because research now suggests that the basilar artery in the brain is not involved in causing its symptoms, as had previously been thought.

While researchers are unsure about precisely how many people have MBA worldwide, a 2006 study of 362 patients with migraine with typical aura (MTA) in Denmark reported that about 1 in 10 of those patients also had MBA (Kirchmann et al., Neurology. 2006; 66(6): 880-886). Another study in China in 2011 found that 6.6% (23/348) of MTA patients had also experienced MBA attacks (Ying et al., Clinical characteristics of basilar-type migraine in the neurological clinic of a university hospital. Pain Medicine). In both studies, there were about 4 times as many women with MBA than men. Most people are initially diagnosed with MBA as teenagers or young adults.

The experience of brainstem aura symptoms can be very distressing and frightening, particularly when they happen for the first time. The symptoms may even cause secondary symptoms like anxiety and hyperventilation, which can make the primary brainstem symptoms more susceptible to misinterpretation or misdiagnosis.

(1) Hence, in a first embodiment, the present invention relates to picotamide, a hydrate or a pharmaceutically acceptable salt thereof for use in the treatment and/or prevention of migraine with aura, wherein in a first period picotamide is administered for 2 to 6 months, followed by a second period of 1 to 3 months without picotamide administration.

Thereby, migraine with aura is diagnosed and defined with the diagnostic criteria (c) above. In particular, the treatment relates to aura attacks.

The advantages of such a dosage regimen with drug holidays is that less drug is necessary, which results in less side effects, better compliance and lower medication costs.

Picotamide can be used as free base in anhydrous form. Moreover, acid addition salts with strong acids are known from WO2008142106. In particular, suitable inorganic acids are, for example, halogen acids, such as hydrochloric or hydrobromic acid, sulfuric acid, or phosphoric acid. Suitable organic acids are, for example, carboxylic, phosphonic, sulfonic or sulfamic acids, for example oxalic acid, maleic acid, amino acids, such as glutamic acid or aspartic acid, methylmaleic acid, dimethylmaleic (citraconic) acid, difluoracetic acid, trifluoroacetic acid, methane- or ethane-sulfonic acid, 2-hydroxyethanesulfonic acid, ethane-1,2-disulfonic acid, 10-camphorsulphonic acid, benzenesulfonic acid, 2-naphthalenesulfonic acid, 1,5-naphthalene-disulfonic acid, o-, m- or p-toluenesulfonic acid, methylsulfuric acid, ethylsulfuric acid, dodecylsulfuric acid, N-cyclohexylsulfamic acid, or N-methyl-, N-ethyl- or N-propyl-sulfamic acid. Preferred picotamide salts are the hydrochloride or the mesylate. Most preferred, however, is picotamide monohydrate.

The term "treatment and/or prevention" in general and for all embodiments means that migraine with aura can be treated and/or prevented with picotamide (or a hydrate or a pharmaceutically acceptable salt thereof), so that there are less migraine and/or aura attacks, and/or the attacks are less strong in comparison to being untreated.

It is to be noted that in this embodiment a first period of picotamide application is followed by a second period which does not involve picotamide application. Thereby, the first period can last from 2 to 6 months and the second period can last from 1 to 3 months.

In further embodiments, the first period lasts from 2 to 5 months, from 2 to 4.5 months, from 2 to 4 months, from 2 to 3.5 months, from 2 to 3 months, from 2 to 2.5 months or just 2 months. In further embodiments the second period lasts from 1 to 2.5 months, from 1 to 2 months, from 1 to 1.5 months or one month. It is to be understood, that each length of the treatment period 1 can be combined with each of the treatment period 2.

(2) In a further embodiment, the sequence of period 1 followed by period 2 is repeated. In one embodiment, they are continuously repeated, until the migraine has disappeared. In one embodiment, they are repeated continuously until the migraine has disappeared, and started again as soon as further migraine attacks start again to appear.

In a further embodiment, the sequence of period 1 followed by period 2 is repeated 7 times, or is repeated 6 times, or is repeated 5 times, or is repeated 4 times, or is repeated 3 times, or is repeated twice. It is to be understood that period 1 as well as period 2 are as defined in (1) or (3).

(3) In a further embodiment, the treatment period 1 is longer than period 2.
  (i) For example, the first period lasts from 2 to 6 months, and the second period lasts from 1 to 3 months, from 1 to 2.5 months, from 1 to 2 months, from 1 to 1.5 months or just one month.
  (ii) For example, the first period lasts from 2 to 5.5 months, and the second period lasts from 1 to 3 months, from 1 to 2.5 months, from 1 to 2 months, from 1 to 1.5 months or just one month.
  (iii) For example, the first period lasts from 2 to 5 months, and the second period lasts from 1 to 3 months, from 1 to 2.5 months, from 1 to 2 months, from 1 to 1.5 months or just one month.
  (iv) For example, the first period lasts from 2 to 4.5 months, and the second period lasts from 1 to 3 months, from 1 to 2.5 months, from 1 to 2 months, from 1 to 1.5 months or just one month.
  (v) For example, the first period lasts from 2 to 4 months, and the second period lasts from 1 to 3 months, from 1 to 2.5 months, from 1 to 2 months, from 1 to 1.5 months or just one month.
  (vi) For example, the first period lasts from 2 to 3.5 months, and the second period lasts from 1 to 2.5 months, from 1 to 2 months, from 1 to 1.5 months or just one month.
  (vii) For example, the first period lasts from 2 to 3 months, and the second period lasts from 1 to 2.5 months, from 1 to 2 months, from 1 to 1.5 months or just one month.
  (viii) Another example would be that the first period lasts from 2.5 to 6 months, from 3 to 6 months, form 3.5 to 6 months, from 4 to 6 months, from 4.5 to 6 months, form 5 to 6 months, from 5.5 to 6 months, or just 6 months. It is to be understood that any one of these first period lengths can be combined with any one of a second period length as described above, in particular in any one as described in (i) to (vii), as long as the second period is shorter than period 1.

(4) In a further embodiment, the present invention relates to picotamide, a hydrate or a pharmaceutically acceptable salt thereof for the use according to embodiments (1) to (3), wherein the migraine with aura is in the range of 3 to 6 aura attacks per month. In this context, patients suffering from 3 to 6 aura/migraine with aura attacks per month are called patients with moderate migraine with aura. This patient group is particularly susceptible to picotamide treatment according to the present invention as can be seen from FIG. 2.

(5) In a further embodiment, the present invention relates to picotamide, a hydrate or a pharmaceutically acceptable salt thereof for the use according to embodiments (1) to (4), wherein the migraine is migraine with typical aura. Thereby, migraine with typical aura and migraine headache are as defined with the diagnostic criteria (d) above.

(6) In a further embodiment, the present invention relates to picotamide, a hydrate or a pharmaceutically acceptable salt thereof for the use according to embodiments (1) to (3), wherein the migraine is hemiplegic migraine. Thereby, hemiplegic migraine and migraine headache are as defined with the diagnostic criteria (e) above.

(7) In a further embodiment, the present invention relates to picotamide, a hydrate or a pharmaceutically acceptable salt thereof for the use according to embodiments (1) to (3), wherein the migraine is migraine with brainstem aura. Thereby, migraine with brainstem aura and migraine headache are as defined with the diagnostic criteria (f) above.

(8) In a further embodiment, the present invention relates to picotamide as a hydrate, in particular a monohydrate, for the use according to embodiments (1) to (7).

(9) In a further embodiment, the present invention relates to picotamide for use according to any one of embodiments (1) to (7), wherein the pharmaceutically acceptable salt is picotamide hydrochloride or picotamide mesylate.

(10) In a further embodiment, the present invention relates to picotamide for use according to any one of embodiments (1) to (9), wherein the treatment dosage is from 200 to 1300 mg (based on free base anhydride) per day.

The treatment dosage of 200 to 1300 mg (based on free base anhydride) per day relates to the treatment period 1, whereby period 2 is free of picotamide administration. Thereby, the dosage during period 1 can be divided in three doses per day or two doses per day, but it can also be once a day. Preferably, the dosage is used once per day, preferably in a sustained-release-form. Preferred doses are 250, 275, 300, 350, 400, 450, 500, 550, 600, 650, 700, 750, 800, 900, 1000, 1100, 1200 or 1300 mg. Particularly preferred are 300, 350, 400, 450, 500, 550, 600, 650, 700, 750, 800, 900, 1000, 1100 or 1200 mg per day. It is to be understood, that each of the given doses may be combined with another given dosage to form a dosage range with a lower and an upper dosage limit. Examples are 200 to 1200 mg, 200 to 1100 mg, 200 mg to 1000 mg, 200 mg to 900 mg, 200 mg to 800 mg, 200 mg to 700 mg.

When referring to numbers, such as e.g. 1.00 and 1 (one), 10.00 and 10 (ten), 100.00 and 100 (one hundred), 1000.00 and 1000 (one thousand), respectively, it is to be understood that according to US format, 1000.00 and 1000 (one thousand) means 1,000.00 and 1,000, respectively, which in other formats is the same as 1,00 and 1 (one), 10,00 and 10 (ten), 100,00 and 100 (one hundred), 1000,00 and 1000 (one thousand), or e.g. 1000.00 and 1,000 (one thousand).

(11) In a further embodiment, the present invention relates to picotamide for use according to any one of embodiments (1) to (9), wherein the treatment dosage is from 200 to 1300 mg based on free base anhydride in a sustained release form. The treatment dosage of 200 to 1300 mg (based on free base anhydride) per day relates to the treatment period 1, whereby period 2 is free of picotamide administration. Particularly preferred doses in period 1 are 250, 275, 300, 350, 400, 450, 500, 550, 600, 650, 700, 750, 800, 900, 1000, 1100, 1200 or 1300 mg. Particularly preferred are 300, 350, 400, 450, 500, 550, 600, 650, 700, 750, 800, 900, 1000, 1100 or 1200 mg per day. It is to be understood, that each of the given doses may be combined with another given dosage to form a dosage range with a lower and an upper dosage limit.

Examples are 200 to 1200 mg, 200 to 1100 mg, 200 mg to 1000 mg, 200 mg to 900 mg, 200 mg to 800 mg, 200 mg to 700 mg. Sustained release dosage forms are designed to release a drug at a predetermined rate in order to maintain a constant drug concentration for a specific period of time with minimum side effects. For instance, the release time may be 24 h. This can be achieved through a variety of formulations, which are commonly known in the field of pharmacology. The term "sustained released" is hereby taken synonymously to "controlled release". It is to be understood, that each of the given doses may be combined with another given dosage to form a lower and an upper dosage limit.

(12) In a further embodiment, the present invention relates to picotamide for use according to any one of embodiments (1) to (9), wherein the treatment dosage is from 200 to 1300 mg free base anhydride provided in a sachet, an orally disintegrating tablet, a chewing tablet, or a lozenge. The treatment dosage of 200 to 1300 mg (based on free base anhydride) per day relates to the treatment period 1, whereby period 2 is free of picotamide administration. Preferred doses in period 1 are 250, 275, 300, 350, 400, 450, 500, 550, 600, 650, 700, 750, 800, 900, 1000, 1100 or 1200 mg. Particularly preferred are 300, 350, 400, 450, 500, 550, 600, 650, 700, 750, 800, 900, 1000, 1100 or 1200 mg per day. It is to be understood, that each of the given doses may be combined with another given dosage to form a dosage range with a lower and an upper dosage limit. Examples are 200 to 1200 mg, 200 to 1100 mg, 200 mg to 1000 mg, 200 mg to 900 mg, 200 mg to 800 mg, 200 mg to 700 mg. Sachets, orally disintegrating tablets, chewing tablets or lozenges as used within the present invention are commonly known in the field of pharmacology.

(13) In a further embodiment, the present invention relates to picotamide for use according to any one of embodiments (1) to (11), wherein the treatment dosage is a once per day dosage. I.e. a dosage of 200 to 1300 mg. The treatment dosage of 200 to 1300 mg (based on free base anhydride) per day relates to the treatment period 1, whereby period 2 is free of picotamide administration. Preferred doses are 250, 275, 300, 350, 400, 450, 500, 550, 600, 650, 700, 750, 800, 900, 1000, 1100 or 1200 mg. Particularly preferred are 300, 350, 400, 450, 500, 550, 600, 650, 700, 750, 800, 900, 1000, 1100 or 1200 mg per day. It is to be understood, that each of the given doses may be combined with another given dosage to form a dosage range with a lower and an upper dosage limit. Examples are 200 to 1200 mg, 200 to 1100 mg, 200 mg to 1000 mg, 200 mg to 900 mg, 200 mg to 800 mg, 200 mg to 700 mg.

(14) In a further embodiment, the present invention relates to a pharmaceutical composition comprising picotamide, a hydrate or a pharmaceutically acceptable salt thereof for the use according to any one of embodiments (1) to (9). The pharmaceutical composition may comprise a pharmaceutically acceptable carrier or excipient, for instance a solid carrier composed of carbohydrates. Carriers or excipients are, for example, sugars, such as mannose, lactose, fructose, glucose, sucrose or saccharose, sugar alcohols, such as mannitol, xylitol or sorbitol, starches, for example corn, wheat, rice or potato starch, cellulose preparations, for example microcrystalline cellulose, methylcellulose, hydroxypropylcellulose, hydroxypropyl methylcellulose, or sodium carboxymethylcellulose, guar gum, carrageenan, acacia gum, polyvinylpyrrolidone, sodium starch glycolate and magnesium stearate. Preferred carriers are microcrystalline cellulose, and in particular hydroxymethylpropylcellulose (HMPC) and sodium carboxymethylcellulose.

(15) In a further embodiment, the present invention relates to a pharmaceutical composition according to embodiment (13), wherein picotamide (based on free base anhydride) is contained from 200 to 1300 mg. Preferred doses are 250, 275, 300, 350, 400, 450, 500, 550, 600, 650, 700, 750, 800, 900, 1000, 1100 or 1200 mg. Particularly preferred are 300, 350, 400, 450, 500, 550, 600, 650, 700, 750, 800, 900, 1000, 1100 or 1200 mg per day. It is to be understood, that each of the given doses may be combined with another given dosage to form a dosage range with a lower and an upper dosage limit. Examples are 200 to 1200 mg, 200 to 1100 mg, 200 mg to 1000 mg, 200 mg to 900 mg, 200 mg to 800 mg, 200 mg to 700 mg.

(16) In a further embodiment, the present invention relates to a pharmaceutical composition according to embodiments (14) and (15), wherein picotamide is contained from 200 to 1300 mg (based on free base anhydride) in a sustained release form. Preferred doses are 250, 275, 300, 350, 400, 450, 500, 550, 600, 650, 700, 750, 800, 900, 1000, 1100 or 1200 mg. Particularly preferred are 300, 350, 400, 450, 500, 550, 600, 650, 700, 750, 800, 900, 1000, 1100 or 1200 mg per day. It is to be understood, that each of the given doses may be combined with another given dosage to form a dosage range with a lower and an upper dosage limit. Examples are 200 to 1200 mg, 200 to 1100 mg, 200 mg to 1000 mg, 200 mg to 900 mg, 200 mg to 800 mg, 200 mg to 700 mg. Sustained release dosage forms are designed to release a drug at a predetermined rate in order to maintain a constant drug concentration for a specific period of time with minimum side effects. For instance, the release time may be 24 h. This can be achieved through a variety of formulations, which are commonly known in the field of pharmacology. The term "sustained released" is hereby taken synonymously to "controlled release". It is to be understood, that each of the given doses may be combined with another given dosage to form a lower and an upper dosage limit.

(17) In a further embodiment, the present invention relates to a pharmaceutical composition according to embodiments (14) to (15), wherein picotamide free base anhydride is contained from 200 to 1300 mg (based on free base anhydride) in a sachet, an orally disintegrating tablet, a chewing tablet or a lozenge. Preferred doses are 250, 275, 300, 350, 400, 450, 500, 550, 600, 650, 700, 750, 800, 900, 1000, 1100 or 1200 mg. Particularly preferred are 300, 350, 400, 450, 500, 550, 600, 650, 700, 750, 800, 900, 1000, 1100 or 1200 mg per day. Sachets, orally disintegrating tablets, chewing tablets or lozenges as used within the present invention are commonly known in the field of pharmacology. It is to be understood, that each of the given doses may be combined with another given dosage to form a dosage range with a lower and an upper dosage limit. Examples are 200 to 1200 mg, 200 to 1100 mg, 200 mg to 1000 mg, 200 mg to 900 mg, 200 mg to 800 mg, 200 mg to 700 mg.

(18) A further embodiment of the present invention relates to the use of picotamide, a hydrate or a pharmaceutically acceptable salt thereof for the manufacture of a pharmaceutical composition for the use in the treatment or prevention of migraine with aura, wherein in a first period picotamide is administered for 2 to 6 months, followed by a second period of 1 to 3 months without picotamide administration. Preferred indications are migraine with typical aura, moderate migraine with aura, hemiplegic migraine, and migraine with brainstem aura.

Preferably, the picotamide is applied from 200 to 1300 mg based on free base anhydride during period 1. Preferred doses are 250, 275, 300, 350, 400, 450, 500, 550, 600, 650, 700, 750, 800, 900, 1000, 1100 or 1200 mg. Particularly preferred are 300, 350, 400, 450, 500, 550, 600, 650, 700, 750, 800, 900, 1000, 1100 or 1200 mg per day. It is to be understood, that each of the given doses may be combined with another given dosage to form a dosage range with a lower and an upper dosage limit.

Examples are 200 to 1200 mg, 200 to 1100 mg, 200 mg to 1000 mg, 200 mg to 900 mg, 200 mg to 800 mg, 200 mg to 700 mg.

In this embodiment, the sequence of period 1 followed by period 2 can be repeated as described in (2). Moreover, treatment period 1 is longer than period 2, as described in (3). A preferred migraine with aura is such a migraine with 3 to 6 aura attacks per month.

(19) A further embodiment of the present invention relates to picotamide, a hydrate or a pharmaceutically acceptable salt thereof as described in (1), for the treatment and/or prevention of migraine with aura, wherein in a first period picotamide is administered for 2 to 6 months, followed by a second period of 1 to 3 months without picotamide administration. Preferred indications are migraine with typical aura, moderate migraine with aura, hemiplegic migraine, and migraine with brainstem aura. Preferably, the picotamide is applied from 200 to 1300 mg based on free base anhydride. Preferred doses are 250, 275, 300, 350, 400, 450, 500, 550, 600, 650, 700, 750, 800, 900, 1000, 1100 or 1200 mg. Particularly preferred are 300, 350, 400, 450, 500, 550, 600, 650, 700, 750, 800, 900, 1000, 1100 or 1200 mg per day. It is to be understood, that each of the given doses may be combined with another given dosage to form a dosage range with a lower and an upper dosage limit. Examples are 200 to 1200 mg, 200 to 1100 mg, 200 mg to 1000 mg, 200 mg to 900 mg, 200 mg to 800 mg, 200 mg to 700 mg.

In this embodiment, the sequence of period 1 followed by period 2 can be repeated as described in (2). Moreover, treatment period 1 is longer than period 2, as described in (3). A preferred migraine with aura is such a migraine with 3 to 6 aura attacks per month.

(20) A further embodiment of the present invention relates to a method of treatment and prevention of migraine with aura, comprising a first period of 2 to 6 months of administering to a patient in need thereof a therapeutically or prophylactically efficient amount of picotamide, a hydrate or a pharmaceutically acceptable salt thereof, followed by a second period of 1 to 3 months without any picotamide administration.

The indications are migraine with aura including migraine with typical aura, moderate migraine with aura, hemiplegic migraine, and migraine with brainstem aura. Preferably, the picotamide, a hydrate thereof or a therapeutically acceptable salt thereof, is administered in period 1 from 200 to 1300 mg based on free base anhydride. Preferred doses are 250, 275, 300, 350, 400, 450, 500, 550, 600, 650, 700, 750, 800, 900, 1000, 1100 or 1200 mg. Particularly preferred are 300, 350, 400, 450, 500, 550, 600, 650, 700, 750, 800, 900, 1000, 1100 or 1200 mg per day. It is to be understood, that each of the given doses may be combined with another given dosage to form a dosage range with a lower and an upper dosage limit. Examples are 200 to 1200 mg, 200 to 1100 mg, 200 mg to 1000 mg, 200 mg to 900 mg, 200 mg to 800 mg, 200 mg to 700 mg.

In this embodiment, the sequence of period 1 followed by period 2 can be repeated as described in (2). Moreover, treatment period 1 is longer than period 2, as described in (3). A preferred migraine with aura is such a migraine with 3 to 6 aura attacks per month.

Examples for such embodiments are:
(20.1) A method of treatment and/or prevention of migraine with aura, said method comprising:
administering, in a first period, picotamide, a hydrate or a pharmaceutically acceptable salt thereof for 2 to 6 months, followed by a second period of 1 to 3 months without picotamide administration.
(20.2) A method of treatment and/or prevention of migraine with aura according to (20.1), said method comprising:
administering, in a first period, picotamide, a hydrate or a pharmaceutically acceptable salt thereof for 2 to 6 months, followed by a second period of 1 to 3 months without picotamide administration, and repeating the sequence of period 1 followed by period 2.

Thereby, the sequence of period 1 followed by period 2 is for instance repeated 7 times, or is repeated 6 times, or is repeated 5 times, or is repeated 4 times, or is repeated 3 times, or is repeated twice. It is to be understood that period 1 as well as period 2 are as defined in (1) or (3).
(20.3) A method of treatment and/or prevention of migraine with aura according to (20.1) or (20.2), wherein period 1 is longer than period 2.
(20.4) A method of treatment and/or prevention of migraine with aura according to (20.1), wherein the migraine with aura is in the range of 3 to 6 aura attacks per month.
(20.5) A method of treatment and/or prevention of migraine with aura according to (20.1) or (20.2), wherein the migraine with aura is migraine with typical aura.

(20.6) A method of treatment and/or prevention of migraine with aura according to (20.1) or (20.2), wherein the migraine with aura is hemiplegic migraine.

(20.7) A method of treatment and/or prevention of migraine with aura according to (20.1) or (20.2), wherein the migraine with aura is migraine with brainstem aura.

(20.8) A method of treatment and/or prevention of migraine with aura according to (20.1) or (20.2), wherein picotamide is a monohydrate.

(20.9) A method of treatment and/or prevention of migraine with aura according to (20.1) or (20.2), the pharmaceutically acceptable picotamide salt is picotamide hydrochloride or picotamide mesylate.

(20.10) A method of treatment and/or prevention of migraine with aura according to (20.1) or (20.2), wherein the treatment dosage is from 200 to 1300 mg based on free base anhydride per day.

Thereby, the treatment dosage of 200 to 1300 mg (based on free base anhydride) per day relates to the treatment period 1, whereby period 2 is free of picotamide administration. Thereby, the dosage during period 1 can be divided in three doses per day or two doses per day. Preferably, the dosage is used once per day, preferably in a sustained-release-form. Treatment doses are 250, 275, 300, 350, 400, 450, 500, 550, 600, 650, 700, 750, 800, 900, 1000, 1100, 1200 or 1300 mg. Preferred are 300, 350, 400, 450, 500, 550, 600, 650, 700, 750, 800, 900, 1000, 1100 or 1200 mg per day. It is to be understood, that each of the given doses may be combined with another given dosage to form a dosage range with a lower and an upper dosage limit. Examples are 200 to 1200 mg, 200 to 1100 mg, 200 mg to 1000 mg, 200 mg to 900 mg, 200 mg to 800 mg, 200 mg to 700 mg.

(20.11) A method of treatment and/or prevention of migraine with aura according to (20.3), wherein the treatment dosage is from 200 to 1300 mg based on free base anhydride per day.

(20.12) A method of treatment and/or prevention of migraine with aura according to (20.4), wherein the treatment dosage is from 200 to 1300 mg based on free base anhydride per day.

(20.13) A method of treatment and/or prevention of migraine with aura according to (20.1) or (20.2), wherein the treatment dosage is from 200 to 1300 mg free base anhydride in a sustained release form.

(20.14) A method of treatment and/or prevention of migraine with aura according to (20.1) or (20.2), wherein the treatment dosage is from 200 to 1300 mg free base anhydride provided in a sachet, an orally disintegrating tablet, a chewing tablet, or a lozenge.

(20.15) A method of treatment and/or prevention of migraine with aura according to (20.1) or (20.2), wherein the treatment dosage is a once per day dosage.

(20.16) A method of treatment and/or prevention of migraine with aura according to (20.3) or (20.4), wherein the treatment dosage is a once per day dosage.

EXAMPLES

A multi-center, randomized, double-blind, placebo controlled crossover study was conducted with picotamide. Patients received either 300 mg picotamide twice daily or matching placebo to evaluate the efficacy and tolerability of picotamide in the prophylaxis of migraine in patients presenting with migraine with aura. The overall study duration was 7×4 weeks.

27 patients (Sequence A) received picotamide for the first 3×4 weeks (Period 1), then 1×4 weeks of placebo (wash-out period), then 3×4 weeks of placebo (Period 2).

"Aura Events" was one of the parameters that was measured. Results were surprising and unexpected and are suggesting that picotamide reduces the number of auras even after picotamide administration.

Figure 2:
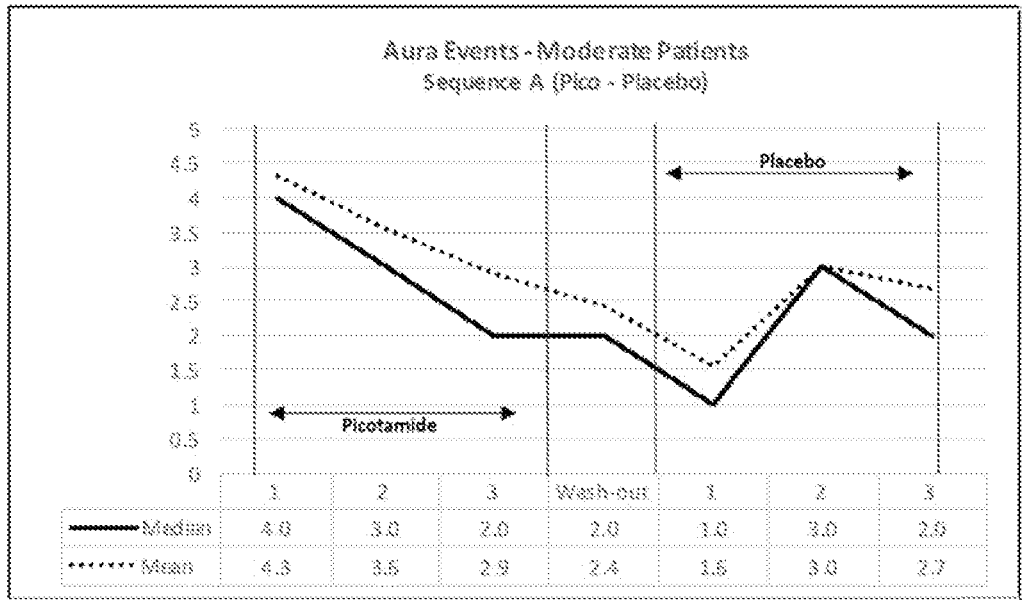
FIG. 2 shows a sequence A, moderate patients (3-6 aura events per month).

These observations were particularly observed in a sub-group of patients (moderate patients) that on average had 3 to 6 aura events per month prior to study enrollment. Patients with less than 3 aura events per month could be considered mild patients and would therefore benefit to a lesser degree from treatment. Patients with 7 or more aura events could be considered severe patients that are difficult to treat. FIG. 2 shows results of aura events for the moderate patients:

FIG. 1: Sequence A, all patients having 1 to 28 aura events per month.

FIG. 2: Sequence A, moderate patients (3-6 aura events per month).

Results:
Data suggest that picotamide has a long-lasting effect on aura events over several weeks after it is discontinued. Patients in Sequence A after having received 3×4 weeks of picotamide continued to improve for another 2×4 weeks despite having switched to placebo.

Numerous modifications and variations on the present invention are possible in light of the above teachings. It is therefore to be understood that within the scope of the described embodiments, the invention may be practiced otherwise than as specifically described herein.

The invention claimed is:

1. A method of treatment of migraine with aura, said method comprising:
   administering, to a patient having or suspected of having migraine with aura, in a first period, picotamide, a hydrate, or a pharmaceutically acceptable salt thereof for 2 to 6 months, followed by a second period of 1 to 3 months without picotamide administration, wherein the migraine with aura is selected from the group consisting of migraine with typical aura, hemiplegic migraine, and migraine with brainstem aura, wherein the sequence of the first period followed by the second period is repeated.

2. The method according to claim 1, wherein the first period is longer than the second period.

3. The method according to claim 1, wherein the migraine with aura is in the range of 3 to 6 aura attacks per month.

4. The method according to claim 1, wherein picotamide is a monohydrate.

5. The method according to claim 1, wherein the pharmaceutically acceptable salt is picotamide hydrochloride or picotamide mesylate.

6. The method according to claim 1, wherein the treatment dosage is from 200 to 1300 mg based on free base anhydride per day.

7. The method according to claim 6, wherein the treatment dosage is from 200 to 1300 mg based on free base anhydride in a sustained release form.

8. The method according to claim 6, wherein the treatment dosage is from 200 to 1300 mg based on free base anhydride provided in a sachet, an orally disintegrating tablet, a chewing tablet, or a lozenge.

9. The method according to claim 6, wherein the treatment dosage is a once per day dosage.

10. A method of treatment of migraine with aura, said method comprising:

administering, to a patient having or suspected of having migraine with aura, in a first period, picotamide, a hydrate, or a pharmaceutically acceptable salt thereof for 2 to 6 months, followed by a second period of 1 to 3 months without picotamide administration, wherein the treatment dosage is from 200 to 1300 mg based on free base anhydride per day, and wherein the treatment dosage is a once per day dosage, wherein the sequence of the first period followed by the second period is repeated.

11. The method according to claim 10, wherein the first period is longer than the second period.

12. The method according to claim 10, wherein the migraine with aura is in the range of 3 to 6 aura attacks per month.

13. The method according to claim 10, wherein picotamide is a monohydrate.

14. The method according to claim 10, wherein the pharmaceutically acceptable salt is picotamide hydrochloride or picotamide mesylate.

15. The method according to claim 10, wherein the treatment dosage is from 200 to 1300 mg based on free base anhydride in a sustained release form.

16. The method according to claim 10, wherein the treatment dosage is from 200 to 1300 mg based on free base anhydride provided in a sachet, an orally disintegrating tablet, a chewing tablet, or a lozenge.

17. A method of treatment of migraine with aura, said method consisting of:

administering, to a patient having or suspected of having migraine with aura, in a first period, picotamide, a hydrate, or a pharmaceutically acceptable salt thereof for 2 to 6 months, followed by a second period of 1 to 3 months without picotamide administration, wherein the migraine with aura is selected from the group consisting of migraine with typical aura, hemiplegic migraine, and migraine with brainstem aura, wherein the sequence of the first period followed by the second period is repeated.

* * * * *